US00PP12065P2

(12) United States Plant Patent
Cully

(10) Patent No.: US PP12,065 P2
(45) Date of Patent: Aug. 28, 2001

(54) SWEET BAY MAGNOLIA TREE NAMED 'JIM WILSON'

(76) Inventor: Earl Cully, R.R. #5, Box 84A, Jacksonville, IL (US) 62650

( * ) Notice: Subject to any disclaimer, the term of this patent is extended or adjusted under 35 U.S.C. 154(b) by 0 days.

(21) Appl. No.: 09/246,188

(22) Filed: Jan. 4, 1999

(51) Int. Cl.[7] ..... A01H 5/00
(52) U.S. Cl. ..... Plt./223
(58) Field of Search ..... Plt./223

(56) References Cited

PUBLICATIONS

Willet N. Wandell, Handbook of Landscape Tree Cultivars, p. 190, 1989.*

* cited by examiner

*Primary Examiner*—Bruce R. Campell
*Assistant Examiner*—Kent L. Bell

(57) ABSTRACT

A new and distinct sweet bay magnolia named 'Jim Wilson' characterized by its distinct upright growth habit, semi-evergreen foliage, fragrant, lemon-scented flowers, and its ability to withstand much lower winter temperatures than trees of the species known to me.

5 Drawing Sheets

The present invention comprises a new and distinct cultivar of sweet bay magnolia, botanically known as *Magnolia virginiana*, and referred to by the cultivar name 'Jim Wilson'.

The initially discovered tree is growing in a cultivated area on the home grounds and arboretum of inventor Earl Cully, Rural Route #5, Box 84A, 846 Hoagland Road, eight miles southeast of Jacksonville, Ill., in Morgan County, in Township 14, Range 10.

The new cultivar 'Jim Wilson' is the result of a selection made from a number of *Magnolia virginiana* seedlings planted in the spring of 1975. All of the seedlings grown in this population were shrubby in habit of growth except two individuals. Of these two trees, one proved to be much superior. This one outstanding individual, now known as the 'Jim Wilson' cultivar, has been evaluated for the past twenty years. It has proven to be an outstanding sweet bay magnolia.

This new cultivar, 'Jim Wilson', is very upright in its growth habit (FIG. 1) and grows with a multiple five stem trunk. The 'Jim Wilson' cultivar is medium oval to vase-shaped in form with a height of thirty-five feet and a limb spread of eighteen feet at twenty-five years of age. Foliage is dark green on the upper surface and silvery-green on the under surface (Figure 5). In most years the tree is evergreen until Christmas in west central Illinois. In a more mild climate, it would probably be evergreen all winter. The 'Jim Wilson' cultivar comes into bloom in late May in central Illinois (depending on the spring season) and gives a good flower display for about thirty days. Flowers are lemon-scented and very fragrant.

The following characteristics in combination distinguish the new tree named 'Jim Wilson' from other non-patented cultivars of *Magnolia virginiana*, including 'Mayer', 'Opelousas', 'Havener', 'Henry Hicks', and 'Croft'.

1. The 'Jim Wilson' cultivar is very cold hardy. It has withstood winter temperatures of −33° F. with no damage! In the spring following this cold temperature, the tree came into leaf and made normal vigorous growth during the growing season. This −33° F. temperature occurred in January 1998 in northern Illinois in a test planting for cold hardiness. During the severe winter of 1977–1978, the 'Jim Wilson', cultivar experienced temperatures of −20° F. with wind chills of −80° F. for long periods of time. The tree suffered no damage from this extreme winter. In October 1991, the temperature was warm for the entire month without any frost to harden plants for winter. On the last day of that month, the temperature dropped into the 'teens. Three days later on November 3, the temperature dropped to −1° F. During that blast of arctic air, some young green ash, along with other hardy tree species, were killed to the ground. The 'Jim Wilson' cultivar did not suffer the slightest damage from this unusual blast of arctic air. The 'Jim Wilson' cultivar would be reliably hardy in all of Zone 5a (USDA Plant Hardiness Zone Map).
2. The 'Jim Wilson' cultivar is highly resistant to wind and ice. It has lost only one limb to wind damage in the years that it has been under test.
3. The 'Jim Wilson' cultivar is adapted to a wide variety of soil types. It will grow in most soils where drainage is good and moisture is adequate.
4. The 'Jim Wilson' cultivar is a vigorous grower. Young asexually propagated trees have made three to four feet of growth in one growing season. These young asexually propagated trees, like the initially discovered tree, all tend to grow with a multi-stem trunk.
5. Flowers are somewhat larger than the species, creamy white (FIG. 4), very fragrant, and bloom for about a month in late spring.
6. The 'Jim Wilson' cultivar, with its semi-evergreen foliage, its upright habit of growth, its cold hardiness, its fragrant floral display in late spring, its adaptability to a variety of soil types, and its rapid, strong growth make it an outstanding small to medium size tree for planting on the home lawn, along city streets, in parks, around the patio, or anywhere a small to medium size tree is needed.

A BRIEF SUMMARY OF THE INVENTION

The 'Jim Wilson' cultivar of *Magnolia virginiana* is very cold hardy, a rapid grower, blooms at a young age (second year after coming out of tissue culture), semi-evergreen in the north, and has an upright medium oval to vase-shaped form. Its use in the landscape is almost limitless.

PROPAGATION

The 'Jim Wilson' cultivar has been successfully asexually propagated in tissue culture, rooting of softwood cuttings, and by chip budding onto *Magnolia kobus*. Propagation is being done at Salem, Oreg.; Olympia, Wash.; McMinnville, Oreg.; and abroad, in Australia. Asexual propagation of the new magnolia by tissue culture in Olympia, Wash. has shown that the unique features of the new magnolia are stable and reproduce true to type in successive generations.

DETAILED BOTANICAL DESCRIPTION

The aforementioned and following observations, measurements, and values describe plants grown near Jacksonville, Ill. The tree used for the description and photographs was about 25 years old.

In the following description, color references are made to The Royal Horticultural Society Colour Chart except where terms of ordinary significance are used.

BRIEF DESCRIPTION OF THE DRAWINGS

The accompanying colored photographs illustrate the appearance and color of the new sweet bay magnolia tree, showing the colors as accurately as is reasonably possible to obtain in colored reproductions of this type. Actual foliage colors may differ slightly from the color values cited in The Plant description due to light reflection.

THE PLANT

Figure 1:
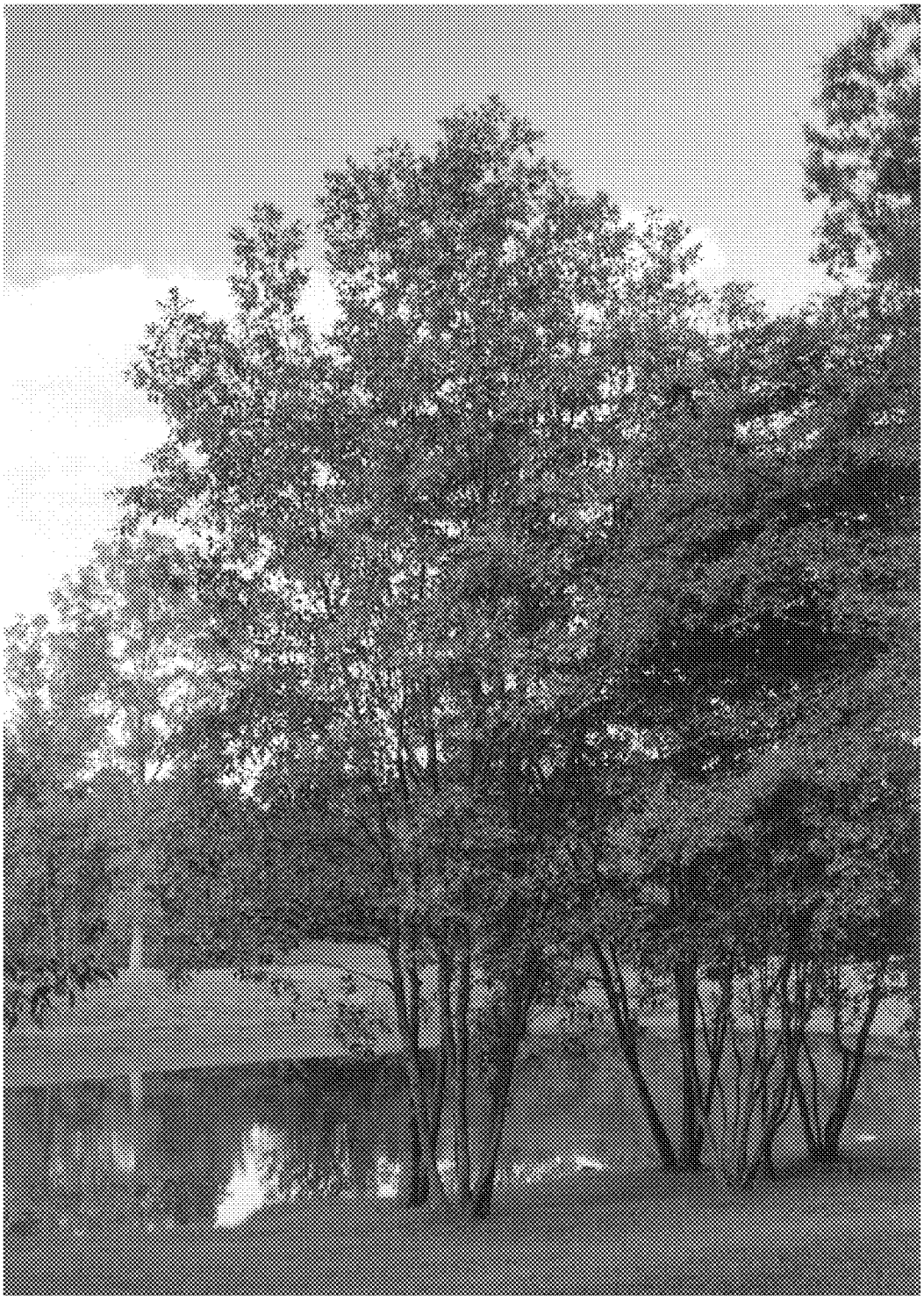
FIG. 1—depicts the initially discovered tree named 'Jim Wilson'.
Figure 2:
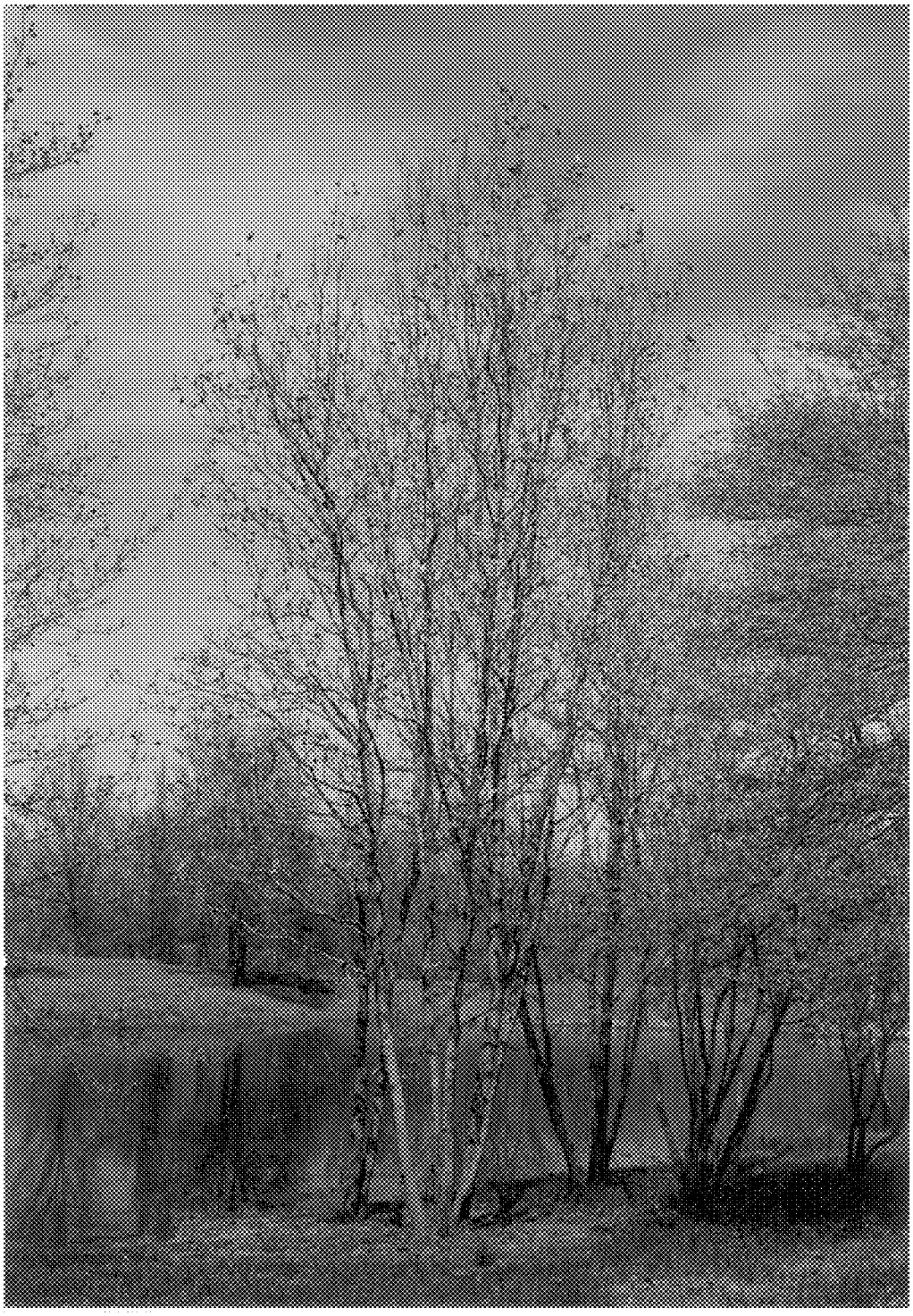
FIG. 2—depicts the 'Jim Wilson' cultivar in early spring after the tree has defoliated and before the new foliage has emerged.
Figure 3:
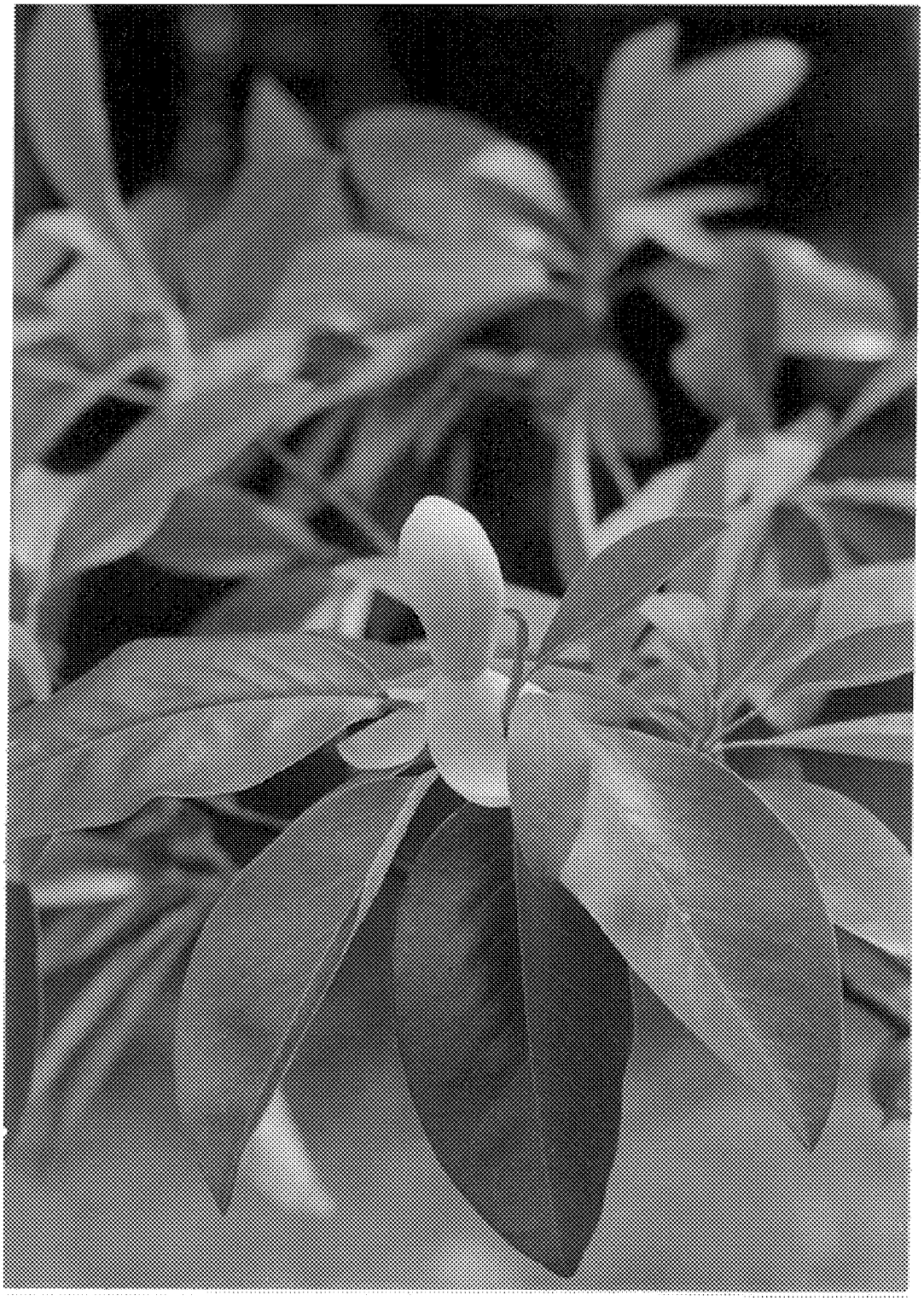
FIG. 3—depicts a typical flower bud before it opens.
Figure 4:
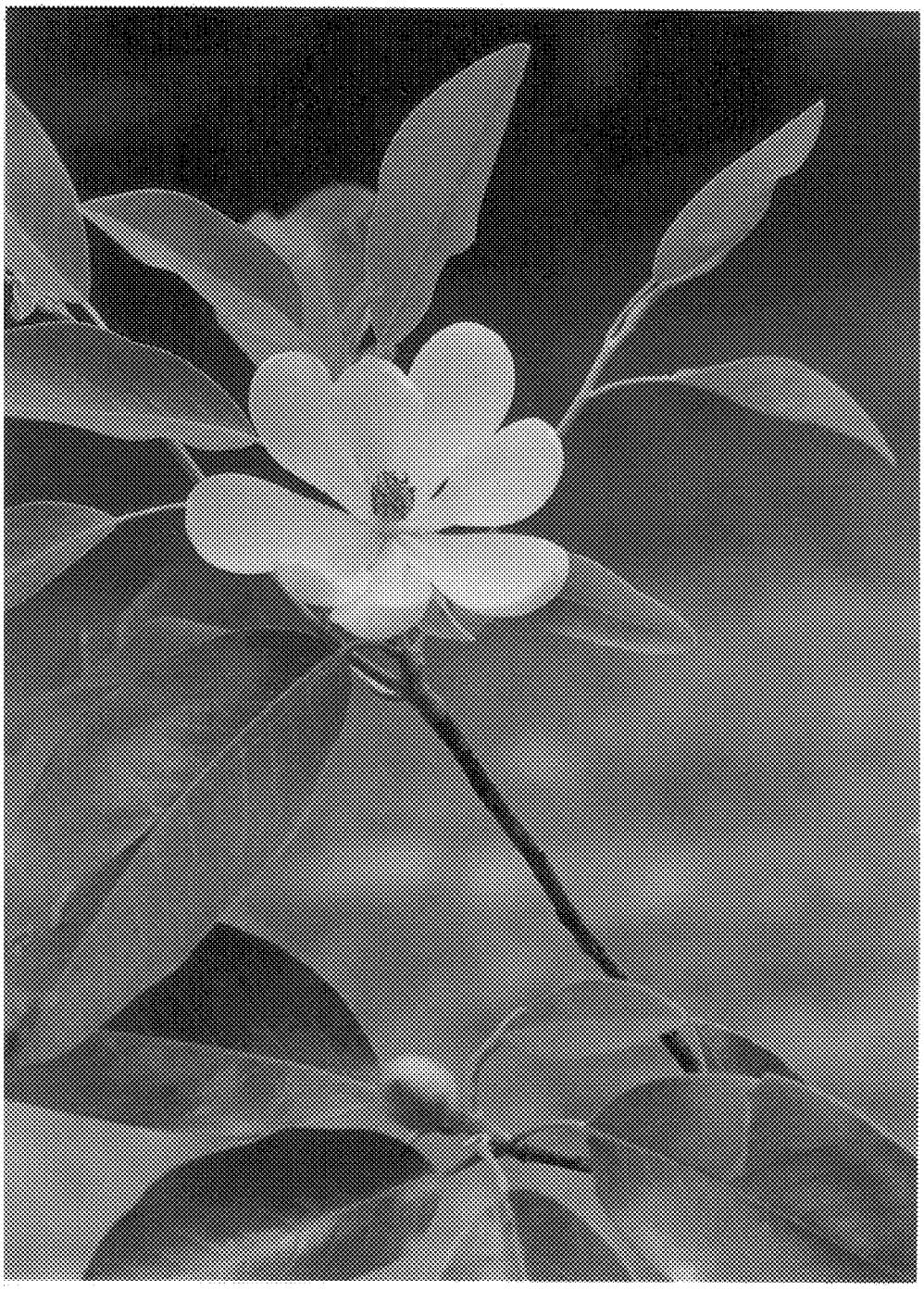
FIG. 4—depicts a typical flower when fully opened (158D RHS).
Figure 5:
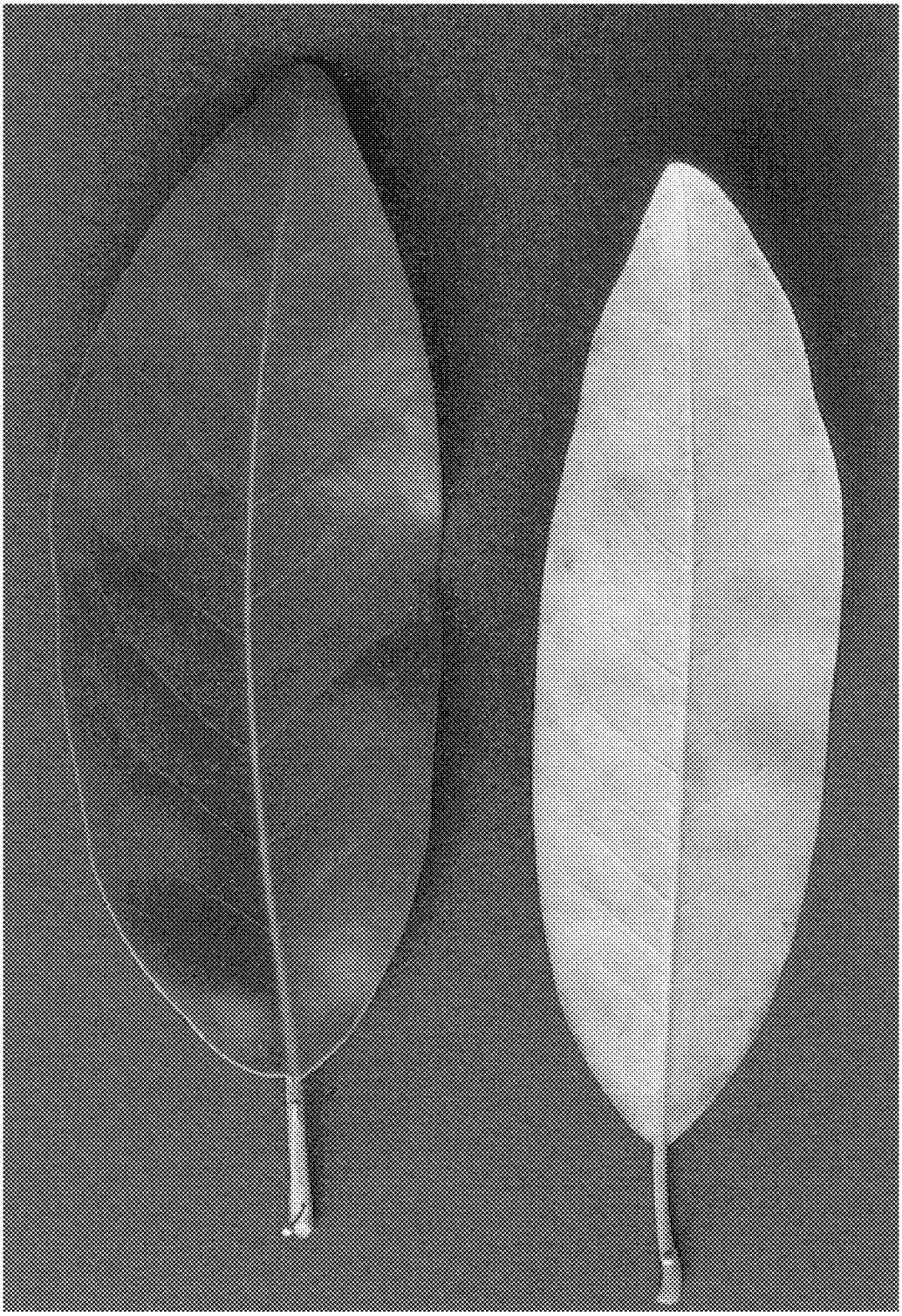
FIG. 5—depicts the color (137A RHS) of the upper surface of a typical leaf, and depicts the color (138C RHS) of the underside of a typical leaf.

Form: Small multi-stem tree.

Shape: Upright, medium oval to vase-shaped.

*Height.*—10.7 m (35') .

*Spread.*—5.5 m (18').

Trunk size (dbh): 5 stems; range 22.9–48.3 cm (9–19") (dbh=diameter at breast height, 4.5' above the ground.

Growth rate: Moderate to fast depending on site.

Strength: Excellent.

Bark (trunk): Bark smooth, about 194A to 201A with splotches of 196A and 199A; textured with small (~1 cm) oval, raised lenticels.

Branches:

*Angle of attachment.*—main trunks stem from ground >60°; most branches between 45° and 80° with a majority >60° from main trunks.

*Spacing.*—Regular.

Size <0.5 cm in diameter:

*Bark.*—Smooth, close to 197A to 199A to 200D with purple 187A rings around twigs at nodes and irregular circular splotches surrounding lenticels; silvery pubescence near leaves at ends of twigs.

*Lenticels.*—Tiny, but conspicuous, silver, slightly raised, oval, 1 mm, surrounded by irregular 187A splotches.

Size >0.5 cm in diameter:

*Bark.*—Smooth, close to 197A to 199A to 200D with purple splotches 187A.

*Lenticels.*—Tiny, inconspicuous.

Leaves: Semi-evergreen.

Length.—Petiole 1.4–2.3 cm, average 1.8 cm (191B RHS); Lamina 7.7–13.5 cm, average 10.4 cm.

*Width.*—2.7–6.0 cm, average 4.5 cm.

*Form.*—Elliptical to lanceolate; base acute to broadly cuneate; apex broadly acute to obtuse.

*Margin.*—Entire.

*Texture.*—Leathery; glossy; glabrous above, silvery-white pubescence beneath.

*Quantity.*—Abundant.

*Color.*—Upper side: dark green (137A RHS). Lower side: silvery-green (138C RHS).

*Ribs and veins.*—Pinnately veined with 11–15 nearly opposite pairs (151A RHS).

Buds: (Vegetative) small (<2 mm in diameter), bluntly pointed, silvery-white pubescence; About 195A to 195B in color.

Flowers:

*Dormant flower buds.*—Terminal, silvery-white pubescence, narrow conical, curved, 3 mm in diameter×17–18 mm long; About 196A to 196B in color.

*Flower.*—Cup-shaped, 10 cm across, creamy white upper surface (158D RHS), (158C lower surface); fragrant, lemon-scented.

*Petals.*—9–12; 4.5–5 cm long, 2–2.5 cm wide; obovate, separate, involute, entire margin, obtuse apex, fused at base.

*Natural blooming season.*—About one month beginning in late May ending in mid June in central Illinois.

*Lastingness of the bloom.*—About one week.

*Stamens.*—Numerous; 3 to 4 mm long; abundant; yellow before anthesis, brown after; self-fertile.

*Pollen amount.*—Moderate.

*Pollen color.*—Yellow.

FRUIT: Subglobose to ellipsoid, light green to brown cone-like aggregate with separate pointed carpels, each with two dark red seeds (42A RHS) 3 cm long and 2.5 cm in diameter.

Disease and pest resistance: No known susceptibility to diseases and pests common to Sweet Bay Magnolias.

It is claimed:

1. A new and distinct cultivar of Sweet Bay Magnolia tree named 'Jim Wilson' as illustrated and described.

* * * * *